(12) United States Patent
Pan et al.

(10) Patent No.: US 9,107,853 B2
(45) Date of Patent: Aug. 18, 2015

(54) COMPOSITIONS CONTAINING PHENOLIC COMPOUNDS AND HYDROTROPES FOR COSMETIC USE

(71) Applicant: L'Oreal S.A., Paris (FR)

(72) Inventors: Zhi Pan, Fort Lee, NJ (US); Jean-Thierry Simonnet, Mamaroneck, NY (US)

(73) Assignee: L'OREAL S.A., Paris (FR)

( * ) Notice: Subject to any disclaimer, the term of this patent is extended or adjusted under 35 U.S.C. 154(b) by 0 days.

(21) Appl. No.: 13/651,038

(22) Filed: Oct. 12, 2012

(65) Prior Publication Data

US 2014/0107048 A1    Apr. 17, 2014

(51) Int. Cl.

| A61K 9/00 | (2006.01) |
|---|---|
| A61K 8/67 | (2006.01) |
| A61Q 19/00 | (2006.01) |
| A61K 8/49 | (2006.01) |
| A61K 31/455 | (2006.01) |
| A61K 31/519 | (2006.01) |
| A61K 31/7048 | (2006.01) |
| A61K 8/368 | (2006.01) |

(52) U.S. Cl.
CPC ................ *A61K 8/676* (2013.01); *A61K 8/368* (2013.01); *A61K 8/498* (2013.01); *A61K 8/4913* (2013.01); *A61K 8/4953* (2013.01); *A61K 8/675* (2013.01); *A61K 31/455* (2013.01); *A61K 31/519* (2013.01); *A61K 31/7048* (2013.01); *A61Q 19/00* (2013.01)

(58) Field of Classification Search
CPC ............. A61K 31/357; A61K 2300/00; C07D 311/32; A01N 2300/00; A61Q 17/04; A61Q 19/00
USPC ....................................................... 424/400
See application file for complete search history.

(56) References Cited

U.S. PATENT DOCUMENTS

| 3,501,409 A | 3/1970 | Matson |
|---|---|---|
| 3,839,210 A | 10/1974 | Beiswanger et al. |
| 4,488,989 A | 12/1984 | Lamberti |
| 4,680,143 A | 7/1987 | Edge et al. |
| 5,532,012 A | 7/1996 | Balentine et al. |
| 5,686,082 A | 11/1997 | N'Guyen |
| 6,121,209 A | 9/2000 | Watts et al. |
| 6,221,823 B1 | 4/2001 | Crisanti et al. |
| 6,331,520 B1 | 12/2001 | Richardson |
| 6,355,657 B1 | 3/2002 | Osborne |
| 6,423,327 B1 | 7/2002 | Dobson, Jr. et al. |
| 6,479,442 B1 | 11/2002 | Berube et al. |
| 6,645,513 B2 | 11/2003 | Dobson, Jr. et al. |
| 6,646,035 B2 | 11/2003 | Koch et al. |
| 6,733,797 B1 | 5/2004 | Summers |
| 6,949,496 B1 | 9/2005 | Boutique et al. |
| 7,452,549 B2 | 11/2008 | Hasler-Nguyen et al. |
| 2002/0086042 A1 | 7/2002 | Delrieu et al. |
| 2002/0110604 A1 | 8/2002 | Babish et al. |
| 2002/0160040 A1* | 10/2002 | Spicer et al. ................... 424/451 |
| 2003/0031715 A1 | 2/2003 | Park et al. |
| 2003/0104080 A1 | 6/2003 | Singh et al. |
| 2003/0206972 A1 | 11/2003 | Babish et al. |
| 2004/0146474 A1 | 7/2004 | Galey |
| 2005/0158271 A1 | 7/2005 | Lee et al. |
| 2005/0266121 A1 | 12/2005 | Lines et al. |
| 2005/0276762 A1 | 12/2005 | Das et al. |
| 2006/0110439 A1 | 5/2006 | Tobia et al. |
| 2007/0065392 A1* | 3/2007 | Simonnet ................... 424/70.31 |
| 2007/0208088 A1 | 9/2007 | Lipshutz |
| 2007/0232561 A1 | 10/2007 | Leung et al. |
| 2008/0095866 A1 | 4/2008 | Declercq et al. |
| 2008/0176956 A1 | 7/2008 | Hsu |
| 2008/0219927 A1 | 9/2008 | Thakur et al. |
| 2009/0110674 A1 | 4/2009 | Loizou |
| 2009/0233876 A1 | 9/2009 | Auriol et al. |
| 2010/0047297 A1 | 2/2010 | Petersen |
| 2011/0033525 A1 | 2/2011 | Liu |
| 2011/0067294 A1 | 3/2011 | Ng et al. |
| 2011/0136245 A1 | 6/2011 | Parker |
| 2011/0152214 A1 | 6/2011 | Boison et al. |
| 2012/0071550 A1 | 3/2012 | Zelkha et al. |

FOREIGN PATENT DOCUMENTS

| DE | 102009037900 A1 * | 8/2009 | ............... A61K 8/49 |
|---|---|---|---|
| JP | 61050918 * | 3/1986 | ............. A61K 31/35 |
| WO | WO-2013016257 A1 | 1/2013 | |

OTHER PUBLICATIONS

Vitamin (http://web.archive.org/web/20120205015610/https://en.wikipedia.org/wiki/Vitamin (downloaded on Jul. 23, 2013)).*
Vitamin E (http://web.archive.org/web/20110918102824/http://en.wikipedia.org/wiki/Vitamin E (downloaded on Jul. 22, 2013)).*
Kanadaswami et al, The Antitumor Activities of Flavonoids, In Vivo, 2005, vol. 19, pp. 895-910.*
JP 61-050918 (English translation by the McElroy Translation Company dated Jan. 2014).*
Yang et al. (Institute of Chinese Materia Medica, 2007, 32, 1996-1999).*
Suzuki, H. et al., "Mechanistic Studies on Hydrotropic Solubilization of Nifedipine in Nicotinamide Solution." *Chem. Pharm. Bull.* 46(1), 125-130 (1998).
Evstigneev, M.P. et al., "Effect of a mixture of caffeine and nicotinamide on the solubility of vitamin (B2) in aqueous solution," *European Journal of Pharmaceutical Sciences* 28, 59-66 (2006).

(Continued)

*Primary Examiner* — Michael G Hartley
*Assistant Examiner* — Melissa Perreira
(74) *Attorney, Agent, or Firm* — Novak Druce Connolly Bove + Quigg LLP

(57) ABSTRACT

Aqueous compositions comprising (a) at least one phenolic compound and (b) at least one hydrotrope in an amount effective to solubilize said at least one phenolic compound in water are provided for cosmetic and other uses.

11 Claims, 1 Drawing Sheet

(56) References Cited

OTHER PUBLICATIONS

Da Silva, R.C. et al., "Investigations on the mechanism of aqueous solubility increase caused by some hydrotropes." *Thermochimica Acta* 328, 161-167 (1999).

Huh, K.M. et al., "A new hydrotropic block copolymer micelle system for aqueous solubililzation of paclitaxel." *Journal of Controlled Release* 126, 122-129 (2008).

Takahashi, K. et al., "Application of hydrotropy to transdermal formulations: hydrotropic solubilization of polyol fatty acid monoesters in water and enchancement effect on skin permeation of 5-FU." *Journal of Pharmacy and Pharmacology* 63, 1008-1014 (2011).

Nicoli, S. et al., "Association of nicotinamide with parabens: Effect on solubility, partition and transdermal permeation." *European Journal of Pharmaceutics and Biopharmaceutics* 69, 613-621 (2008).

Nidhi, K. et al., "Hydrotropy: A Promising Tool for Solubility Enhancement: A Review." *International Journal of Drug Development & Research* 3(2), 26-33 (2011).

Notification of Transmittal of the International Search Report and the Written Opinion of the International Searching Authority, or the Declaration; International Search Report; Written Opinion of the International Searching Authority, International Application No. PCT/US2013/064466, dated Feb. 21, 2014.

\* cited by examiner

COMPOSITIONS CONTAINING PHENOLIC COMPOUNDS AND HYDROTROPES FOR COSMETIC USE

BACKGROUND OF THE INVENTION

The present invention relates to aqueous compositions comprising at least one phenolic compound and at least one hydrotrope, for cosmetic use.

The formation of free radicals is a widely accepted pivotal mechanism leading to skin aging. Free radicals are highly reactive molecules with unpaired electrons that can directly damage various cellular membranes, lipids, proteins, RNA and DNA. The damaging effects of these reactive oxygen species are induced internally during normal metabolism and externally through various oxidative stresses. UV exposure and environmental pollution can accelerate skin aging by producing free radicals in skin. Antioxidants protect cells from the damage of oxidative stress by scavenging free radicals and inhibiting following oxidation reactions. The topical application of antioxidants is broadly used in skin care product to prevent skin aging.

Phenol/polyphenols, the most abundant antioxidants in diet, are well known as very effective anti-oxidants. They have been widely studied in the prevention of degenerative diseases, particularly cardiovascular diseases and cancers. Many phenol/polyphenols have been formulated in nutrition supplement and consumer products. However, the solubility of most phenol/polyphenols is very limited, especially in water, which diminishes their applications and biological potential in cosmetics. Thus, there is a need for methods of increasing the water solubility of phenol/polyphenols.

Applications and biological potential of many phenol/polyphenols in cosmetics are limited due to their poor solubility. Various delivery systems, such as gel carriers (US application publication 20020086042), or nano crystals (US application publication 2010/0047297), or chemical modification of the polyphenols (US application publications 20090233876, 20080095866, and 20080176956) have been used to obtain better solubility of phenol/polyphenols. However, these approaches have drawbacks. Some are tied to specific delivery systems. Modification of phenol/polyphenols increases costs, the improvement of solubility is still limited, and modifications can reduce the activity of the phenol/polyphenols.

Other solutions to the problem of poor solubility include the use of solubilizers such as strong organic solvents (U.S. Pat. No. 5,532,012) and diterpene glycosides (US application publication 2011/0033525). Nevertheless, these solutions do not have good safety, and are not necessarily compatible with cosmetic formulations. Moreover, most of the time, when water is added to such compositions, the solubility of the phenol/polyphenols decreases dramatically.

Thus, there remains a need for methods for improving the water solubility of phenolic compounds, including polyphenols, for cosmetic and other uses.

BRIEF SUMMARY OF THE INVENTION

The invention provides aqueous compositions comprising (a) at least one phenolic compound and (b) at least one hydrotrope in an amount effective to solubilize said at least one phenolic compound in water. The hydrotrope can be a cosmetically acceptable hydrotrope, such as nicotinamide, caffeine, sodium PCA, sodium salicylate, urea, or hydroxyethyl urea. The phenolic compound can be any type of phenol or polyphenol.

Another aspect of the invention provides a method for preparing an aqueous composition comprising including in said composition at least one phenolic compound and at least one hydrotrope in an amount sufficient to solubilize said phenolic compound in water.

A further aspect of the invention provides a method comprising applying an aqueous composition to skin, the aqueous composition comprising (a) at least one phenolic compound and (b) at least one hydrotrope in an amount effective to solubilize the at least one phenolic compound in the water phase.

These and other aspects of the invention are set out in the appended claims, and described in greater detail in the detailed description of the invention.

DETAILED DESCRIPTION OF THE INVENTION

Figure 1:
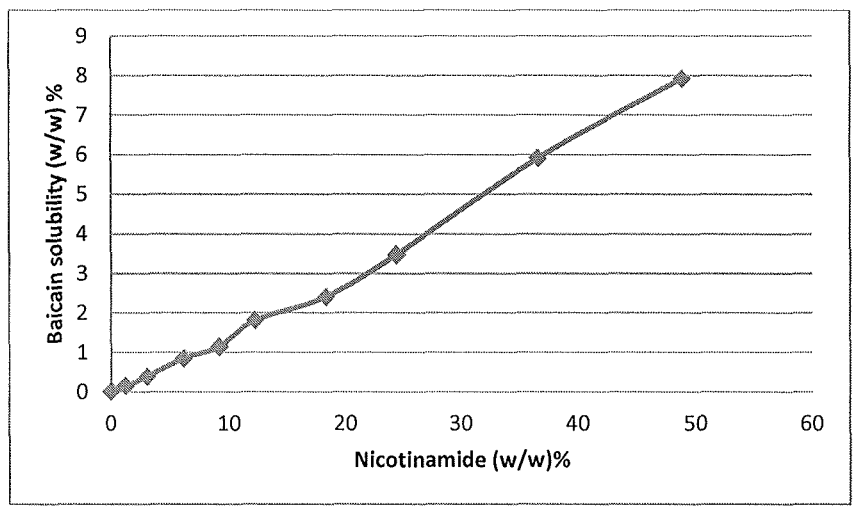
FIG. 1 shows a graph of baicalin solubility as a function of nicotinamide concentration.

The present invention provides aqueous compositions comprising at least one phenolic compound and at least one hydrotrope for cosmetic and other uses. The hydrotrope, such as a cosmetically acceptable hydrotrope, improves the water solubility of the phenolic compound. The hydrotropes can be used to formulate phenolic compounds, especially polyphenols, in all cosmetic formulas that contain water, for topical application or injection, and food applications, such as beverages.

Most phenolic compounds, including polyphenols, have very limited solubility (<0.1%) in water depending on their various structures. Applicants have discovered that hydrotropes can dramatically increase the solubility of these poorly water soluble phenolic compounds in water by orders of magnitude. The aqueous compositions thus contain phenolic compounds in greater percentage amounts than aqueous compositions in which the hydrotrope is not present. Applicants have also found that combinations of hydrotropes, such as the combination of caffeine and nicotinamide, is more efficient that either one alone for increasing the water solubility of phenolic compounds.

Hydrotropes (or hydrotropic agents) are a diverse class of water-soluble compounds that characterized by an amphiphilic molecular structure and ability to dramatically increase the solubility of poorly soluble organic molecules in water.

Most hydrotropes have aromatic structure with an ionic moiety, while some of them are linear alkyl chains, as listed in the table below. Although hydrotropes noticeably resemble surfactants and have the ability to reduce surface tension, their small hydrophobic units and relatively shorter alkyl chain distinguish them as a separate class of amphiphiles. Consequently their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Lee S. et al., "Hydrotropic Polymers: Synthesis and Characterization of Polymers Containing Picolylnicotinamide Moieties", Macromolecules, 36, 2248-2255, 2003.

Cosmetically acceptable hydrotropes refers to hydrotropes that can be used in cosmetic compositions. While hydrotropes represent a broad class of molecules used in various fields, cosmetic applications will be limited due to safety and tolerance restrictions. Suitable hydrotropes for use in cosmetics include, but are not limited to, the hydrotropes listed below:

| Name of hydrotropes | Structure |
|---|---|
| Nicotinamide (Vit B3) | 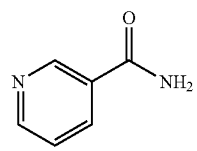 |
| Caffeine | 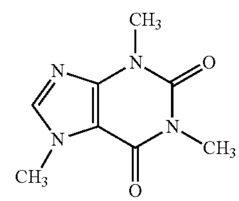 |
| Sodium PCA | 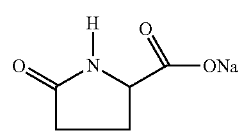 |
| Sodium Salicylate | 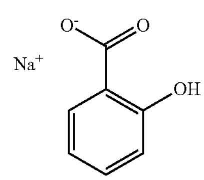 |
| Urea | 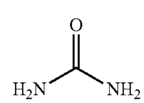 |
| Hydroxyethyl urea | 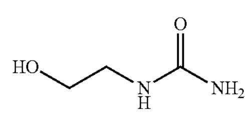 |

The suitability of a hydrotrope for use in cosmetic compositions can be determined using tests known in the art for determining effects on skin, and toxicity to humans.

At least one hydrotrope refers to one or a combination of two or more hydrotropes. One or combination of two or more hydrotropes can be used to improve the solubility of phenolic compounds in water.

The at least one hydrotrope is present in the aqueous composition in amounts effective to increase the solubility of the phenolic compound in water. The amount of hydrotrope will vary depending on the hydrotrope and the type and amount of phenolic compound. The amount of hydrotrope present in the aqueous compositions can range from about 0.1% to about 20%; about 0.1% to about 10%; or about 1% to about 50%, based on the total weight of the composition.

Increasing the water solubility of the phenolic compound(s) refers to increasing the solubility of the phenolic compound(s) in water in comparison with solubility of the phenolic compound(s) in water in the absence of the hydrotrope or hydrotropes.

An advantage of using hydrotropes is, once a stable solution is obtained, further dilution doesn't influence the stability of the solution. This is very different from organic solvents that are commonly used to increase the water solubility of phenolic compounds, such as polyphenols. Typically, an aqueous dilution of organic solvents with pre-dissolved phenolic compound(s), such as a polyphenol, results in crystallization or precipitation.

Phenolic compounds are a structural class of natural, synthetic, and semisynthetic organic compounds that have one or more phenolic constituents. Phenolic compounds containing multiple phenol groups are known as polyphenols. Polyphenols are normally available in plants and are very helpful to protect plants and also animals from usual health disorders and also the impacts of aging. Polyphenols function as potent free radical scavengers by donating their alcoholic hydrogen or one of their delocalized electrons. The two classes of polyphenols are flavonoids and non-flavonoids.

Flavonoids are a specific group of polyphenols, and are the most plentiful group of polyphenol compounds, making up about two-thirds of the total phenols in consumed feed. Flavonoids are further categorized, according to chemical structure, into chalcones, flavones, flavanones, flavanols, flavonols, dihydroflavonols, isoflavonoids, neoflavonoids, catechins, anthocyanidins, and tannins. Over 4,000 flavonoids have been identified, many of which occur in fruits, vegetables and beverages (tea, coffee, beer, wine and fruit drinks). The flavonoids have been reported to have antiviral, anti-allergic, antiplatelet, anti-inflammatory, antitumor and antioxidant activities. Flavonoids protect lipids and vital cell components from damaging oxidative stress by efficiently scavenging free radicals.

Non-flavonoid polyphenols include lignans, aurones, stilbenoids, curcuminoids and other phenylpropanoids. Many of them are also well-known antioxidants like resveratrol, curcumin, and pinoresinol.

Other phenolic compounds, in addition to polyphenols, include alkylphenols, betacyanins, capsacinoids, hydroxybenzoketones, methoxyphenols, naphthoquinones, and phenolic terpenes. Some popular examples are ferulic acid, hydroxytyrosol, cinnamic acid, caffeic acid, and p-coumaric acid.

The at least one phenolic compound is solubilized in the aqueous compositions, and the amount of phenolic compound will depend on the specific phenolic compound and the type and amount of hydrotrope present in the aqueous compositions. The amount of phenolic compound present in the aqueous compositions can range from about 0.01% to about 20%; about 0.1% to about 20%; or about 0.1% to about 10%, based on the total weight of the composition.

The aqueous compositions can also comprise at least one additive conventionally used in the cosmetics field which does not affect the properties of the compositions according to the invention, such as thickeners, fragrances, pearlescent agents, preservatives, sunscreens, anionic or nonionic or cationic or amphoteric polymers, proteins, protein hydrolysates, fatty acids, such as 18-methyleicosanoic acid, vitamins, panthenol, silicones, vegetable, animal, mineral or synthetic oils, gelling agents, antioxidants, solvents, fragrances, fillers, screening agents, odor absorbers and coloring materials. These additives can be present in the composition according to the invention in proportions which are not limited, but which advantageously fall in the range from 0 to 50% by weight, with respect to the total weight of the composition.

The composition comprises from about 1 to 99.9% by weight of water, with respect to the total weight of the composition. The amount of water in the composition can range from about 1 to 99.5%; about 1 to 60%; or about 1 to 50%, based on the total weight of the composition.

The pH of the aqueous compositions is not limited but is generally between 2 and 12, or between 3 and 9. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Generally, any composition of the invention can be ingested, injected or topically applied to the skin (over any cutaneous region of the body) or to the mucous membranes (oral, jugal, gingival, genital, conjunctival, and the like). Depending on the method of administration under consideration, the composition can be provided in any dosage form normally used.

For topical application to the skin, the composition can have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type, or else of microcapsules or microparticles, or of vesicular dispersions of ionic and/or nonionic type or of foams. These compositions are prepared according to the usual methods.

For injection, the composition can be provided in the form of aqueous or oily lotions or in the form of serums. For the eyes, the composition can be provided in the form of drops and, for ingestion, it can be provided in the form of capsules, granules, syrups or tablets.

The amounts of the various constituents of the compositions according to the invention are those conventionally used in the fields under consideration.

In the cosmetics field, these compositions constitute in particular creams for cleaning, protecting, treating or caring for the face, for the hands, for the feet, for the major anatomical folds or for the body (for example, day creams, night creams, make-up-removing creams, foundation creams or sun creams), liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, after-shave gels or lotions, depilatory creams, compositions for countering insect stings or bites, pain-relieving compositions or compositions for treating certain skin diseases, such as eczema, rosacea, psoriasis, lichen and severe pruritus.

Another aspect of the invention provides a method for preparing the aqueous compositions comprising including in the composition at least one phenolic compound and at least one hydrotrope in an amount sufficient to solubilize the phenolic compound, such as a polyphenol, in water. A hydrotrope solution is prepared by completely dissolving one or more hydrotropic agents into water. Phenolic compound(s) compounds are then added in and mixed using stirring bar or any other mixer. Solubilization of the phenolic compound occurs within minutes and mixing continued until the maximum concentration achieved, which was defined as the solubility of the phenolic compound(s) under that condition. A clear stable solution with a concentration that does not exceed the solubility would be ready after more than one hour of mixing. No heat is necessary by following this procedure to dissolve phenolic compounds. Everything is prepared at room temperature to keep the stability of phenolic compounds. This is extremely useful to protect the activity of certain compounds and also makes the process much easier.

EXAMPLES

Example 1

Baicalin, a component of Chinese medicinal herb Huang-chin, is a flavone, a type of flavonoid. It is a potent antioxidant that demonstrates potent effects against oxidative stress diseases, inflammation, allergy, cancer, bacterial infections, etc. However, its solubility in water is extremely low (<0.01% at its natural pH~4.5), especially at low pH, as shown below, and degradation happens at pH>5.

| | PH | | | | |
|---|---|---|---|---|---|
| | 3 | 3.5 | 4 | 4.5 | 5 |
| solubility | 0.0016% | 0.0021% | 0.0040% | 0.0084% | 0.035% |

Although certain organic solvents can increase the solubility of baicalin, such as PEG-4 which can dissolve 3% baicalin, a dilution of these solutions in water is not stable any more. Crystallization or precipitation occurs after mixing the glycol phase and water phase.

The solubility of baicalin can be increased by raising the concentration of hydrotropes. And unlike in organic solvents, such solutions are still stable if diluted in water.

Water solubility of baicalin was increased as a function of nicotinamide concentration as shown in FIG. 1.

Figure 2:
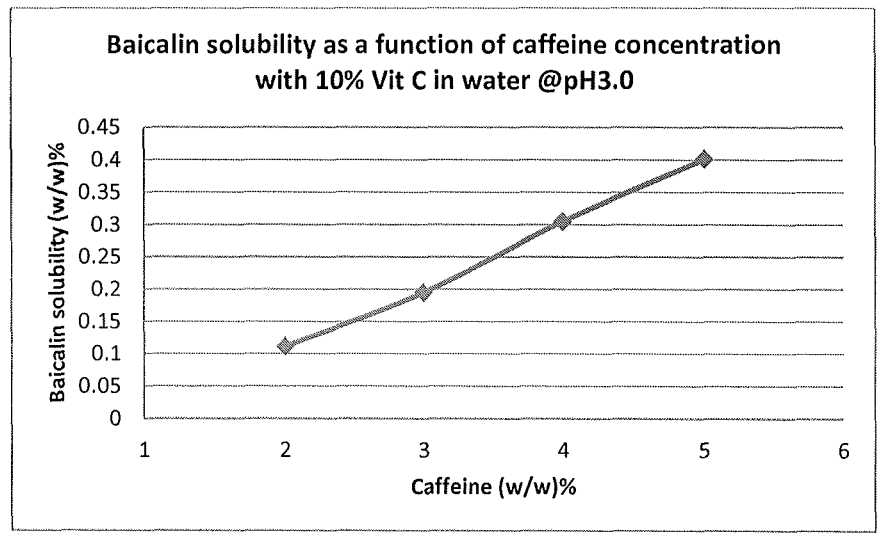
FIG. 2 shows a graph of baicalin solubility as a function of caffeine concentration.

2% (w/w) caffeine in water improved the water solubility of baicalin from <0.01% to 0.11%; and further improvement was observed as more caffeine was dissolved in water with 10% Vit C, shown in FIG. 2.

Example 2

Combination of Nicotinamide and Caffeine

The water solubility of caffeine is approximately 2%, which limited its function as a hydrotropic agent. By mixing with nicotinamide, the solubility of caffeine can be increased to 5% or higher. And the combination of caffeine and nicotinamide is more efficient than any one of themselves. The combination of 5% nicotinamide and 5% caffeine in water solubilized approximately 1% baicalin in water, which dramatically increased the water solubility of baicalin by more than 100 times.

After the hydrotrope solution was prepared at certain concentrations by completely dissolving one or more hydrotropic agents into water, phenolic compounds were added in and mixed using stirring bar or any other mixer, solubilization happened in minutes and kept going on till the maximum concentration achieved, which was defined as the solubility of the phenolic compound under that condition. A clear stable solution with a concentration that does not exceed the solubility would be ready after >1 hour mixing. No heat is necessary by following this procedure to dissolve phenolic compounds. Everything is prepared at room temperature to keep the stability of the phenolic compounds. This is extremely useful to protect the activity of certain compounds and also makes the process much easier.

The association of hydrotropes, 5% nicotinamide and 5% caffeine, have been found to be very efficient to increase the water solubility of numerous polyphenols, including flavonoid and non-flavonoid polyphenols, and other phenolic compounds.

The results are listed in the table below:

| Phenolic compoundl | Type | Solubility in water without hydrotropes %(w/w) | Solubility in water with hydrotropes %(w/w) |
|---|---|---|---|
| Baicalin | flavones | <0.01 | >1 |
| Taxifolin | dihydroflavonols | <0.1 | >1 |
| Neohesperidin | dihydrochalcone | <0.05 | >1 |
| Resveratrol | stilbenoids | <0.005 | >0.75 |
| Ellagic acid | tannins | <0.001 | >0.01 |
| Ferulic acid | Phenolic acid | <0.1 | >2 |

Example 3

Compatibility of the Polyphenol/Hydrotrope Complex in Different Systems

Preparation A: Serum

| Phase | Component | Weight % of total |
|---|---|---|
| A | Propylene glycol | 10 |
| A | Dipropylene glycol | 10 |
| A | Ethanol | 10 |
| B | Water | 59.5 |
| B | Nicotinamide | 5 |
| B | Caffeine | 5 |
| B | Baicalin | 0.5 |

Preparation A was prepared as follows. The glycol phase (Phase A) components were mixed together at room temperature. At the same time, the aqueous phase (Phase B) components were mixed at room temperature until a clear solution was obtained. The glycol phase was then added into the aqueous phase with constant stirring for another one hour, and the desired serum was obtained.

Preparation B: O/W Emulsion (Cream)

| Phase | Component | Weight % of total |
|---|---|---|
| A1 | Water | 58.5 |
| A1 | Nicotinamide | 5 |
| A1 | Caffeine | 5 |
| A1 | Baicalin | 0.5 |
| A2 | Glycerin | 10 |
| A2 | Xanthan gum | 0.2 |
| A2 | Preservatives | 1 |
| B | Dicaprylyl carbonate | 3 |
| B | Dimethicone | 3 |
| B | Dicapryl alcohol and ceteareth-20 | 4 |
| B | Glyceryl stearate and PEG-100 stearate | 4.5 |
| C | Dimethicone ammonium | 4 |
| C | Polyacryloyldimethyl taurate | 0.3 |
| D | Nylon-12 | 1 |

Preparation B was prepared as follows. Phase A1 components were mixed at room temperature till clear solution was obtained. In separate containers, Phase A2 was pre-suspended and then added into Phase A1 with constant stirring and heated to 65° C. At the same time, Phase B components were mixed and completely dissolved at 65° C. Then Phase B was added into Phase A and emulsified for 10-15 minutes. Heating was stopped, and mixing was continued when Phase C was added and mixed for another 10 minutes. Phase D was added after the temperature was below 40° C., and mixed for 10-15 minutes (side sweep) or until powders were fully dispersed, and the desired emulsion was obtained.

Preparation C: W/Si Emulsion (Gel)

| Phase | Component | Weight % of total |
|---|---|---|
| A | BIS-PEG/PPG-14/14 DIMETHICONE (and) DIMETHICONE | 4 |
| A | Dimethicone (and) dimethiconol | 1 |
| A | Dimethicone | 10 |
| B1 | Water | 43.95 |
| B1 | Nicotinamide | 5 |
| B1 | Caffeine | 5 |
| B1 | Baicalin | 0.5 |
| B2 | Glycerin | 15 |
| B2 | Propylene glycol | 5 |
| B3 | Water | 5 |
| B3 | Preservatives | 0.25 |
| B3 | Sodium citrate | 0.2 |
| B3 | Sodium chloride | 0.8 |
| C | Ethanol | 3 |
| C | Preservatives | 0.6 |
| D | Silica silylate | 0.7 |

Preparation C was prepared as follows. Phase A components were mixed together at room temperature. Phase B1 and Phase B2 were premixed in separate containers at room temperature until clear solutions were obtained. Phase B3 was mixed while heating it to 75-80° C. until it was clear. Phase B2 and Phase B3 were added into Phase B1 while mixing. Then Phase B was slowly added into Phase A while mixing (as viscosity increased, the mixing speed was appropriately increased). When the addition was finished, mixing was continued for an additional 10 minutes before adding pre-mixed Phase C. Phase D was slowly added while mixing till it was thoroughly dispersed, and the desired emulsion was obtained.

What is claimed is:

1. A skin care product in the form of an oil-in-water (O/W), water-in-oil (W/O), or water-in-silicon (W/Si) emulsion comprising:
   (a) about 0.1 wt. % to about 1 wt. % of baicalin;
   (b) about 1 wt. % to about 60 wt. % of water; and
   (c) about 0.1 wt. % to about 5 wt. % nicotinamide and about 0.1 wt. % to about 5 wt. % of caffeine.

2. The skin care product according to claim 1, wherein the pH of the product is 5 or less.

3. The skin care product according to claim 1, further comprising:
   (d) dimethicone; and
   (e) glycerin.

4. The skin care product of claim 1 comprising:
(c) about 5 wt. % nicotinamide and about 5 wt. % of caffeine.

5. The skin care product according to claim 4, further comprising:
(d) dimethicone; and
(e) glycerin.

6. The skin care product according to claim 5, further comprising:
(f) dicapryl alcohol, ceteareth-20, glyceryl stearate, and/or PEG-100 stearate.

7. A skin care product in the form of an oil-in-water (O/W), water-in-oil (W/O), or water-in-silicon (W/Si) emulsion comprising:
(a) about 0.1 wt. % to about 10 wt. % of at least one polyphenol selected from the group consisting of taxifolin, neohesperidin, resveratrol, ellagic acid, and ferulic acid;
(b) water; and
(c) about 0.1 wt. % to about 5 wt. % nicotinamide and about 0.1 wt. % to about 5 wt. % of caffeine.

8. The skin care product according to claim 7 in the form of an oil-in-water (O/W) or water-in-oil (W/O) emulsion.

9. The skin care product according to claim 7 in the form of a water-in-silicon (W/Si) emulsion.

10. The skin care product according to claim 7, further comprising:
(d) dimethicone;
(e) glycerin; and
(f) dicapryl alcohol, ceteareth-20, glyceryl stearate, and/or PEG-100 stearate.

11. The skin care product of claim 7 comprising:
(c) about 5 wt. % nicotinamide and about 5 wt. % of caffeine.

* * * * *